United States Patent
Nakasone et al.

(10) Patent No.: US 7,120,007 B2
(45) Date of Patent: Oct. 10, 2006

(54) ION GENERATING UNIT

(75) Inventors: Hidetoshi Nakasone, Hikone (JP); Itaru Saida, Hikone (JP); Kengo Ito, Hikone (JP)

(73) Assignee: Matsushita Electric Works, Ltd., Osaka (JP)

( * ) Notice: Subject to any disclaimer, the term of this patent is extended or adjusted under 35 U.S.C. 154(b) by 204 days.

(21) Appl. No.: 10/879,021

(22) Filed: Jun. 30, 2004

(65) Prior Publication Data

US 2005/0117269 A1    Jun. 2, 2005

(30) Foreign Application Priority Data

Jul. 31, 2003    (JP) ............................. 2003-284192

(51) Int. Cl.
- H01T 23/00 (2006.01)
- H05F 7/02 (2006.01)
- F41B 15/04 (2006.01)
- G03G 15/02 (2006.01)
- H05F 3/02 (2006.01)
- H01H 47/00 (2006.01)

(52) U.S. Cl. ............... 361/231; 361/232; 361/235; 361/212; 361/220

(58) Field of Classification Search .......... 361/231, 361/232, 235, 212, 220
See application file for complete search history.

(56) References Cited

U.S. PATENT DOCUMENTS

| 6,653,638 | B1 * | 11/2003 | Fujii .................. 250/423 R |
| 2002/0062836 | A1 | 5/2002 | Saida et al. |

* cited by examiner

Primary Examiner—Stephen W. Jackson
Assistant Examiner—Dharti H. Patel
(74) Attorney, Agent, or Firm—Rader, Fishman & Grauer PLLC

(57) ABSTRACT

An ion generating unit is made compact, yet avoids the undesired arc discharge for successfully generating the ions. The ion generating unit includes a dielectric base having a length and carrying a needle electrode and a ground electrode. The needle electrode has a pointed tip and is adapted to receive a high electric voltage relative to the ground electrode for electrically charging particles present in the surrounding air. The dielectric base being a polyhedron having multiple faces including a first face and a second face which are different from each other and have the length of the dielectric base. The needle electrode is mounted on or in a closely adjacent relation to the first face, and has its pointed tip directing forwardly along the length of the dielectric base with the pointed tip receded from the front end of the base. The ground electrode is mounted at the front end of the base in longitudinally spaced relation with the pointed tip. The ground electrode include anchor ends only by which the ground electrode is secured to the base. The anchor ends are fixed to the second face of the base, but not to the first face. Thus, the creepage distance between the electrodes extends over the first face and also the second face of the dielectric base, thereby being given an elongated distance relative to the air path between the electrodes for successfully generating the ions.

4 Claims, 7 Drawing Sheets

HIGH VOLTAGE GENERATING CIRCUIT

ION GENERATING UNIT

TECHNICAL FIELD

The present invention is directed to an ion generating unit for generating ions in the surrounding air by developing the corona discharge around a needle electrode receiving a high voltage relative to an associated ground electrode.

BACKGROUND ART

European Patent Publication EP 1 208 766 A2 discloses a like ion generating unit that includes a needle electrode and a ground electrode for developing the corona discharge to generate the ions in the air around the pointed tip of the needle electrode by applying a high voltage across the electrodes. The unit has a dielectric tube which surrounds the needle electrode and the ground electrode in the form of arc or partially cut ring. The needle electrode is held in a center of the dielectric tube, while the ground electrode is disposed at one longitudinal end of the tube in a longitudinally spaced relation to the pointed tip of the needle electrode. However, the use of the tube necessitates a dead space at a portion of the tube away from the ground electrode. For making the unit compact, it could be theoretically possible to make the wall of the tube closer to the needle electrode. However, due to the structural limitation that the needle electrode and the ground electrode are supposed to be mounted in any manner commonly on the inner face of the tube, the above approach might bring about a problem of shortening a creepage distance between the needle electrode and the ground electrode along the common inner face of the tube. When the creepage distance becomes greater than an air path between the pointed tip of the needle electrode and the ground electrode, a harmful arc discharge instead of the corona discharge would certainly develop therebetween the electrodes, failing to generate the ions. Thus, the above approach alone is found unsuccessful to make the whole unit more compact.

DISCLOSURE OF THE INVENTION

In view of the above problem or insufficiency, the present invention has been accomplished to proved an ion generating unit which is capable of being made compact, yet avoiding the undesired arc discharge for successfully generating the ions. The ion generating unit in accordance with the present invention includes a dielectric base having a length and carrying a needle electrode and a ground electrode. The needle electrode has a pointed tip and is adapted to receive a high electric voltage relative to the ground electrode for electrically charging particles present in the surrounding air. The needle electrode has a voltage terminal for electrical connection with a voltage output of an external high voltage generating circuit. The ground electrode has a ground terminal for electrical connection with a ground of the high voltage generating circuit. The dielectric base being a polyhedron having multiple faces including a first face and a second face which are different from each other and have the length of the dielectric base. The needle electrode is mounted on or in a closely adjacent relation to the first face, and has its pointed tip directing forwardly along the length of the dielectric base with the pointed tip receded from the front end of the dielectric base. The ground electrode is mounted at the front end of the dielectric base in longitudinally spaced relation with the pointed tip of the needle electrode. The ground electrode is formed to include anchor ends only by which the ground electrode is secured to the dielectric base. The anchor ends are fixed to the second face of the dielectric base, not to the first face. Thus, the creepage distance between the needle electrode and the ground electrode extends over the first face and also the second face of the dielectric base, thereby being given an elongated distance relative to the air path between the electrodes for successfully generating the ions by developing the corona discharge, while enabling to mount the needle electrode as close as possible to the upper face of the dielectric base for making the whole unit compact.

Preferably, the base is designed to include a generally flat plate which defines the first and second faces respectively on top and bottom thereof. The dielectric base further includes a pair of side ribs integrally upstanding from the lateral edges of the plate. In this version, the ground electrode is shaped into an arched member with a pair of inward bents that extend integrally from the lower ends of the arched member to define the anchor end. The inward bents are fixed to the second face, i.e., the bottom of the plate with the lower ends of the arched member routing outwardly of the side ribs. With the inclusion of the side ribs, the creepage distance is further elongated to ensure the corona discharge for successfully generating the ions, yet assuring the compact structural design of the unit.

Further, the dielectric base is preferred to have on its upper face a socket for retaining the needle electrode. The socket has a slot into which the needle electrode is inserted with its pointed tip projecting from the socket. The slot is defined between a pair of partitions which are integrally supported by the side ribs in an upwardly spaced relation to the upper face of the dielectric base, and is configured to receive the needle electrode in such a manner as to float the needle electrode above the upper face of the base. Thus, the needle electrode can be held close to the upper face of the base, yet further elongating the creepage distance by way of the partitions.

In order to exactly position the needle electrode in relation to the ground electrode, it is preferred that that the needle electrode is formed at its intermediate portion with a U-shaped bent to be fitted into a bottom open cavity in the slot.

Still further, a dielectric cap may be press-fitted on the socket for fixing the needle electrode to the socket.

In another preferred version, the dielectric base is shaped into a generally flat plate that defines the first and second faces respectively on the top and bottom thereof. The needle electrode is mounted on the upper face of the plate, while the ground electrode is mounted on the lower face so as not to project onto the upper face, thereby elongating the creepage distance between the electrodes.

Further, the dielectric base may be shaped into a generally flat plate that defines the first face by one of side faces of the plate and the second face collectively by upper face, lower face, and the other side face of the plate. Also in this case, the creepage distance is elongated by mounting the needle electrode on the one side face, and by mounting the ground electrode to bridge over the upper face, the lower face, and the other side face of the plate.

These and still other advantageous features of the present invention will become apparent from the following description of the preferred embodiments when taken in conjunction with the attached drawings.

BEST MODES FOR CARRYING OUT THE INVENTION

Figure 1:
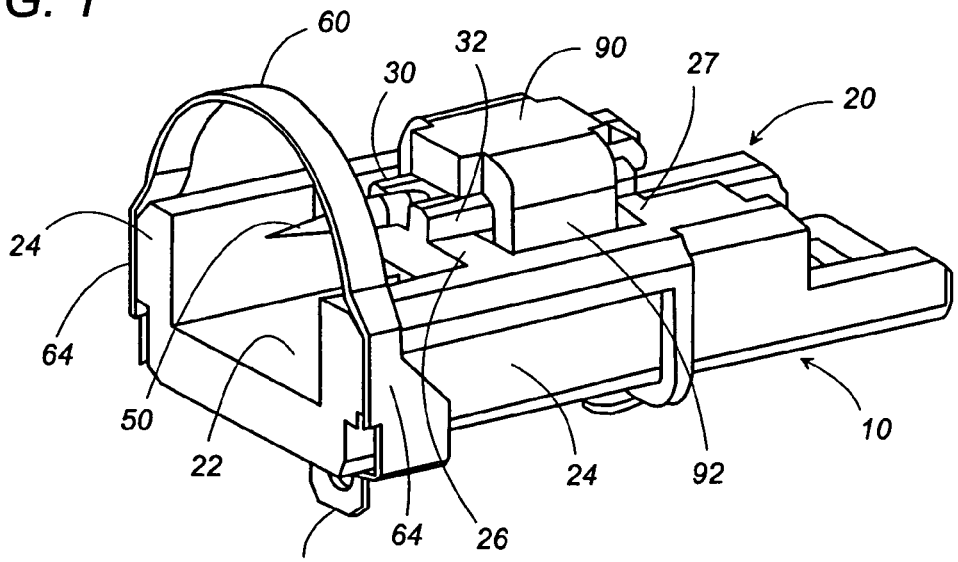
FIG. 1 is a perspective view of an ion generating unit in accordance with a preferred embodiment of the present invention.
Figure 2:
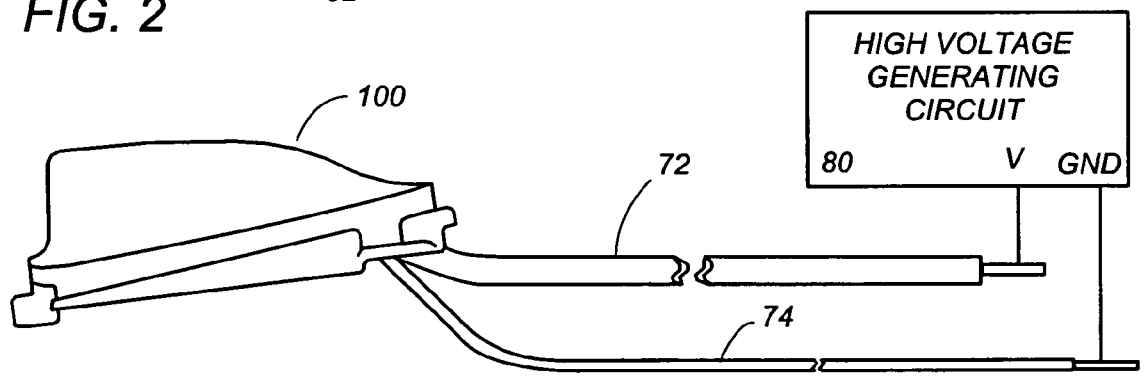
FIG. 2 is a front view of the unit with a cover attached.
Figure 3:
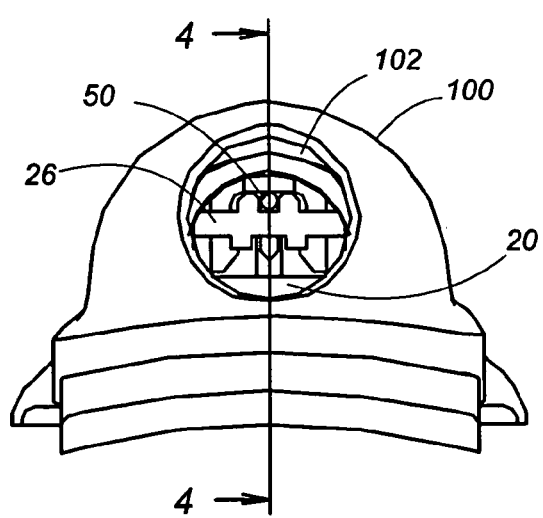
FIG. 3 is a side view of the unit with the cover attached.

Referring now to FIGS. 1 to 6, there is shown an ion generating unit in accordance with a preferred embodiment of the present invention. The ion generating unit 10 includes a dielectric base 20 which is molded from an electrically insulating plastic material into a generally flat rectangular configuration for carrying a needle electrode 50 and a ground electrode 60. The base 20 includes a bottom plate 22, side ribs 24 upstanding from the lateral edges of the plate 22, and a socket 30 holding the needle electrode 50. The needle electrode 50 has a pointed tip at its front end and is provided at its rear end with a voltage terminal 52 for soldering connection with a wire 72 leading to a voltage output of a high voltage generating circuit 80. The needle electrode 50 is aligned with the length of the base 20 and is disposed at a width center of the base 20 with its pointed tip receded from the front edge of the base 20. The ground electrode 60 is disposed at the front end of the base in a forwardly spaced relation to the pointed tip of the needle electrode 50 and is provided with a ground terminal 62 for soldering connection with a ground wire 74 leading to a ground of the high voltage generating circuit 80. The high voltage generating circuit 80 applies a high voltage, for example, −5 kV to the needle electrode 50 relative to the ground electrode 60, thereby developing the corona discharge between the electrodes to negatively charge the particles present in the surrounding air for generating negatively charged ions around the pointed tip of the needle electrode 50. The ions are attracted towards the ground electrode 60 to move in a forward direction past the ground electrode 50 and is caused to emit through a front opening 102 of a cover 100 fitted over the base 20. The cover 100 is molded from a dielectric plastic material and is fixed to the base 20 by snap engagement therewith.

Figure 4:
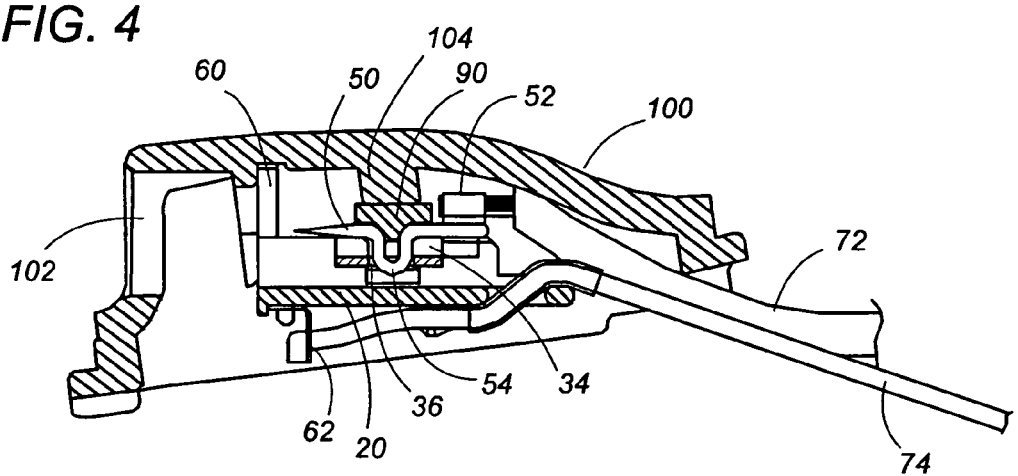
FIG. 4 is a section taken along line 4—4 of FIG. 3.
Figure 8:
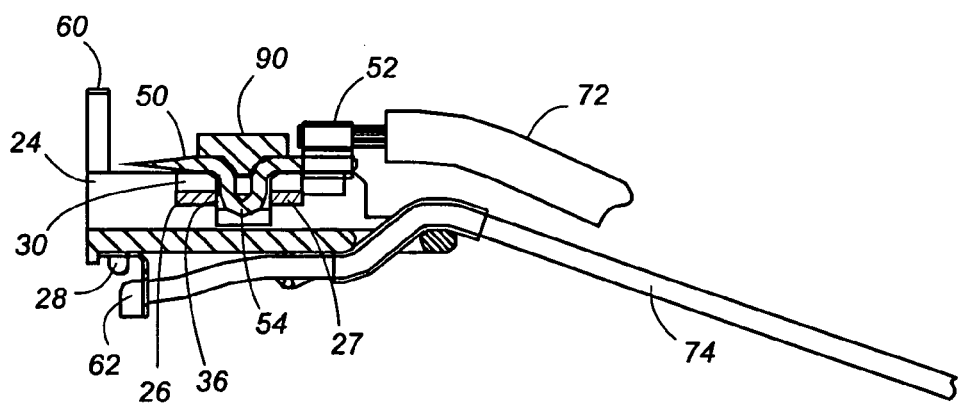
FIG. 8 is a section taken along line 8—8 of FIG. 7.
Figure 9:
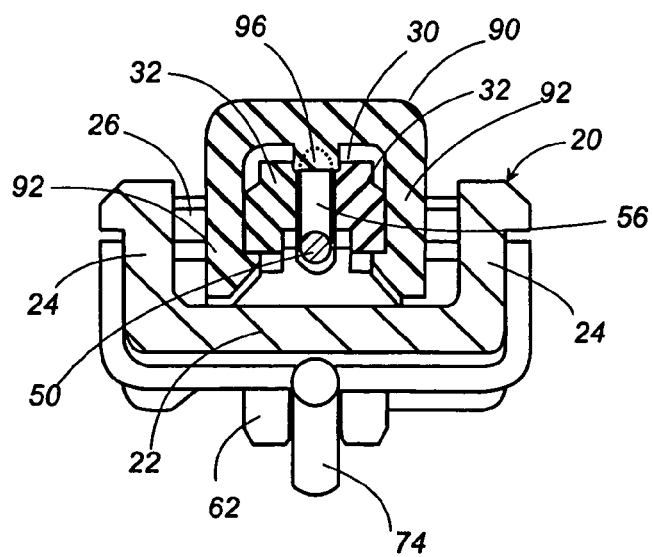
FIG. 9 is a section taken along line 9—9 of FIG. 7.

As shown in FIGS. 4, 5, 7 and 9, the socket 30 includes a pair of partitions 32 which are supported by front and rear beams 26 and 27 each bridging the side ribs 24 in a spaced relation with respect to the length of the base 20. The beams 26 and 27 as well as the partitions 32 are spaced upwardly of the plate 22 to leave an open space on the upper face of the plate 22. It is within a slot 34 formed between the partitions 32 that the needle electrode 50 is received in such a manner as to project its pointed tip outwardly of the socket 30. The slot 34 is opened at a portion between the front and rear beams 26 and 27 to define thereat a bottom open cavity 36. The cavity 36 receives a U-shaped bent 56 of the needle electrode 50 to retain the needle electrode in an accurate position relative to the ground electrode 60, as best shown in FIGS. 4 and 8. The U-shaped bent 56 is formed intermediate the length of the needle electrode 50 and has its lower end kept in out of direct contact relation, i.e., in a floating relation to the upper face of the plate 22. A cap 90 made of a dielectric material is snapped on the socket 30 to retain the needle electrode 50. The cap 90 has a pair of legs 92 which are hooked with the lower ends of the partitions 32, as shown in FIG. 9, with a projection 96 on the inner top bottom of the cap 90 engaged into a recess of the U-shaped bent 56 to fix the needle electrode 50 to the socket 30. In this connection, a bulge 104 on the interior wall of the cover 100 is held against the cap 90, as shown in FIG. 4, for maintaining the secure and precise mounting of the needle electrode 50 to the base 20.

Figure 5:
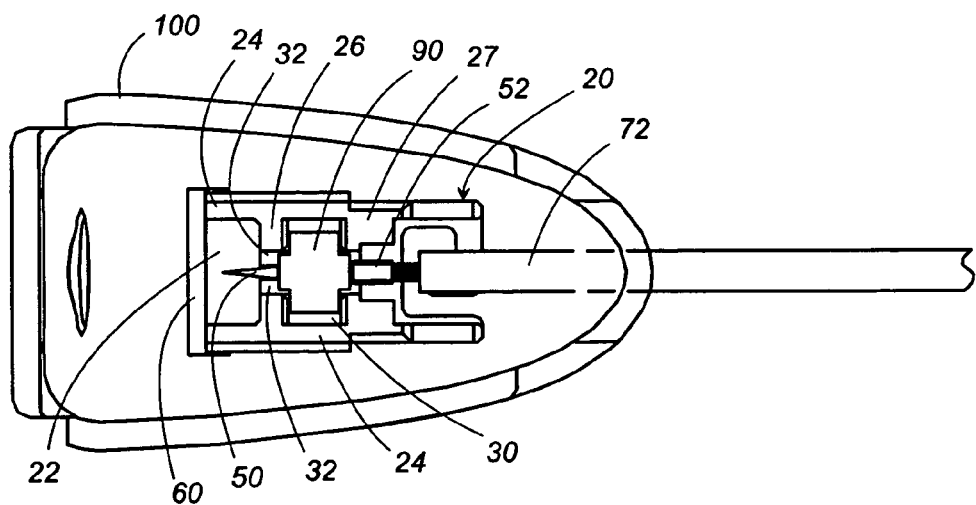
FIG. 5 is a top view of the unit with a portion of the cover removed.
Figure 6:
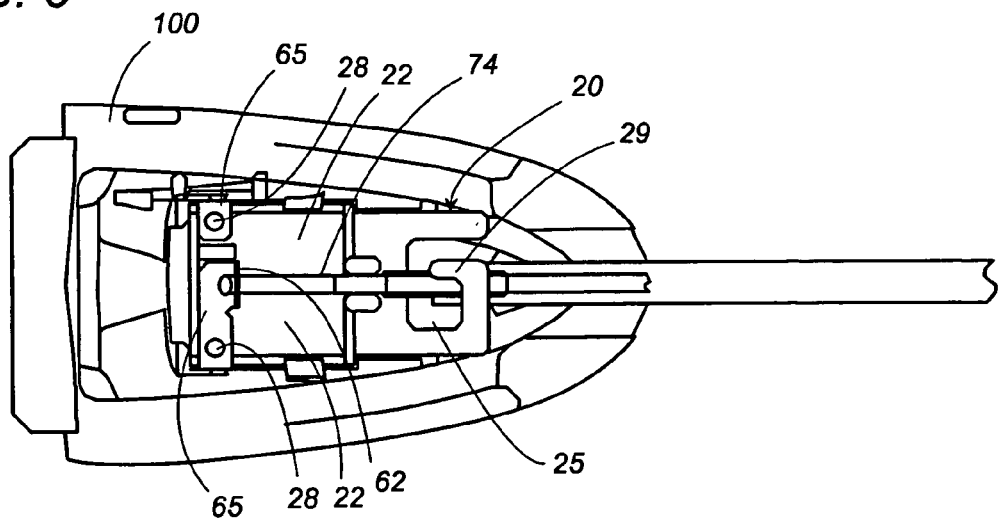
FIG. 6 is a bottom view of the unit.
Figure 7:
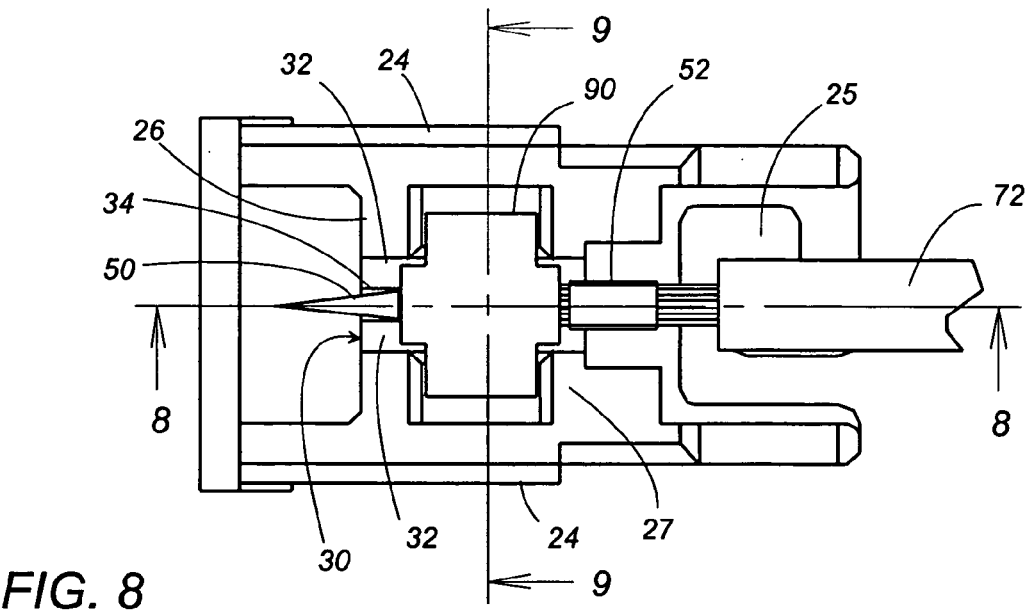
FIG. 7 is a top view of the unit with the cover removed.

Turning back to FIG. 1, the ground electrode 60 is bent into an arch-shape member having a pair of limbs 64 which are routed around the side ribs 24 at the front end of the base 20. As best shown in FIG. 6, the lower end of each limb 64 includes an inward bent 65 which defines an anchor end by which the ground electrode 60 is fixed to the bottom of the base 20. Each inward bent 65 is formed with a hole receiving a stud 28 on the bottom of the base 29 for securing the ground electrode 60 to the base 20. The ground electrode 60 is secured to the front end of the base only at the inward bents 65. The ground terminal 62 extends integrally from one of the bents 65 to project on the outer bottom of the base 20 for connection with the wire 74. Since the ground terminal 60 is fixed to the bottom of the plate 22 which is a different face from the upper face of the plate 22 carrying the needle electrode 50, the ground electrode 60 is kept away from the ground electrode 50 in terms of a creepage distance, thereby realizing effective insulation therebetween to avoid the undesired arc discharge which would be detrimental to the ion generation. The creepage distance is elongated also by the interposition of the side ribs 24 between the electrodes 50 and 60, and further by the floating support of the needle electrode 50 above the plate 22 of the base 20. As shown in FIGS. 4 to 6, the base 20 is formed at its rear end with an opening 25 through which the wire 74 from the ground electrode 60 is routed from the underside to the upper face of the base 20 so as to be gathered with the wire 72. The opening 25 is formed with a hook 29 for secure engagement of the wire 74 to the base.

Figure 10:
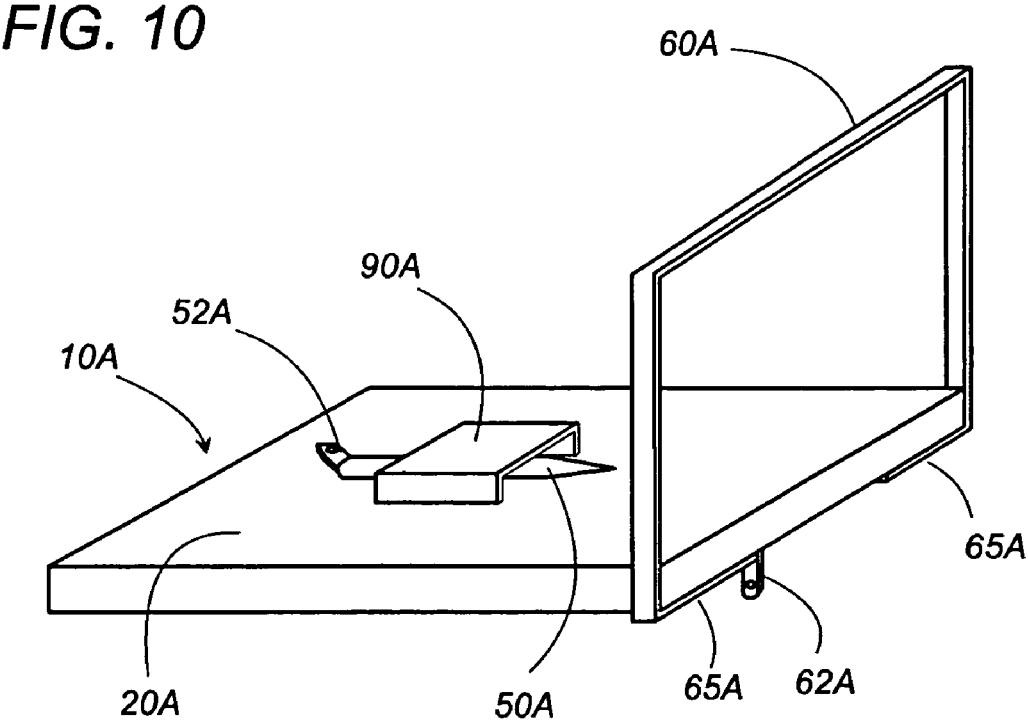
FIG. 10 is a perspective view of an ion generating unit in accordance with another embodiment of the present invention.
Figure 11:
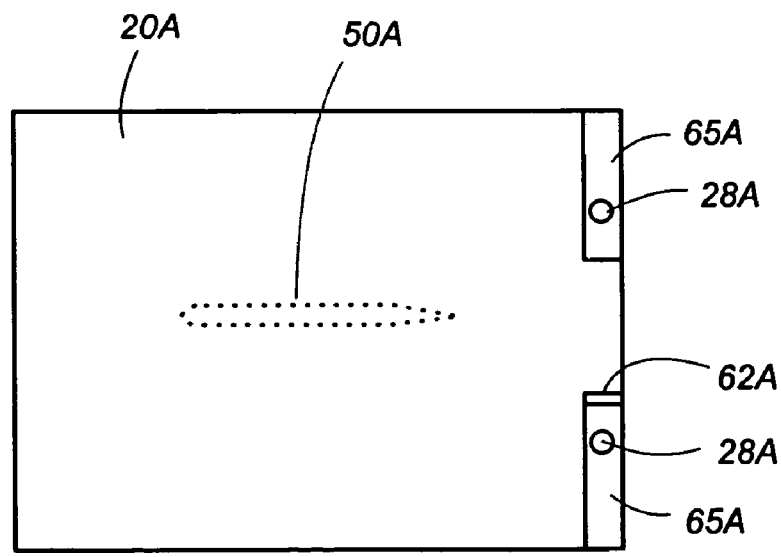
FIG. 11 is a bottom view of the above unit.

FIGS. 10 and 11 illustrate, in a rather schematic representation, an ion generating unit 10A in accordance with another preferred embodiment of the present invention. Like parts are designated by like reference numerals with a suffix letter of "A" for an easy reference purpose. The unit includes a dielectric base 20A in the form of a flat rectangular plate having multiple faces including the upper face, lower face, and the side faces. A needle electrode 50A is supported on the upper face of the base 20A, whereas a ground electrode 60A is mounted at the front end of the base 20A. The needle electrode 50A is mounted in the lateral center of the base 20A and is aligned with the length of the base 20A with its pointed tip receded from the front end of the base. A voltage terminal 52 is provided at its rear end for connection with a wire leading to the voltage output of a like high voltage generating circuit as utilized in the previous embodiment. A dielectric cap 90A is fitted over the needle electrode 50A to fix the same on the upper face of the base 20A, while exposing the pointed tip in a floating relation to the upper face of the base. The ground electrode 60A is shaped into a square configuration with its lower ends bent over the lower face of the base 20A to define like inward bents 65A which are fixed in the like manner as in the previous embodiment, i.e., by engagement with corresponding studs 28A on the lower face of the base 20A. A ground terminal 62A is bent downward from one of the bents 65A for connection with a wire leading to the ground of the high voltage generating circuit. Also in this embodiment, the ground electrode 60A is fixed to the base 20A only at the lower face different from the upper face of the base 20A to be given an elongated creepage distance between the electrodes along the surface of the base 20A.

Figure 12:
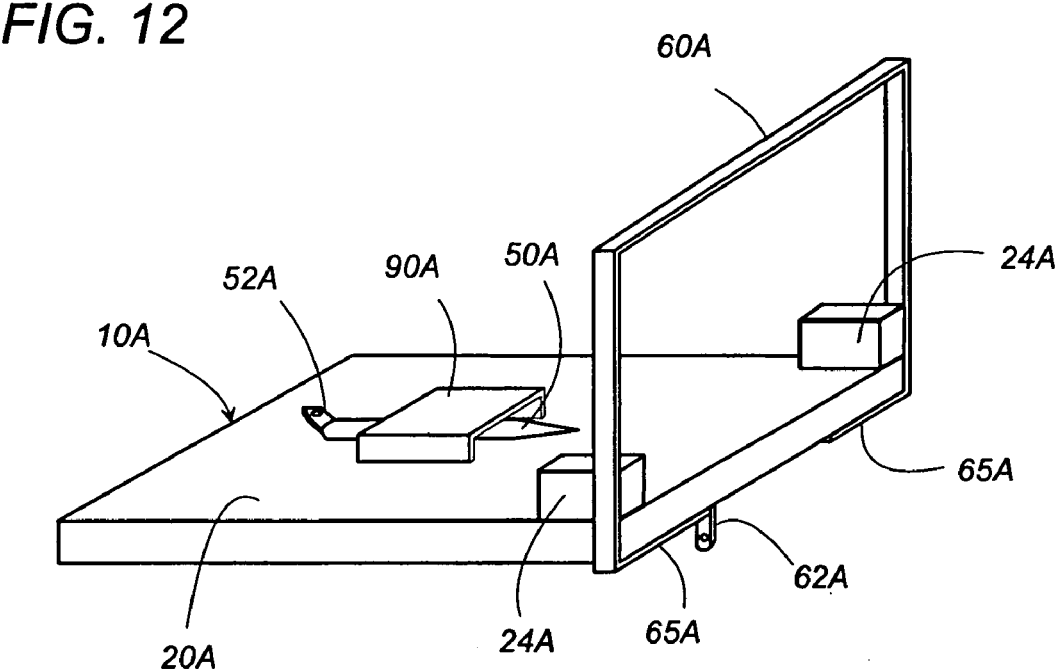
FIGS. 12 to 15 are perspective views respectively illustrating ion generating units respectively in accordance with further embodiments of the present invention.
Figure 13:
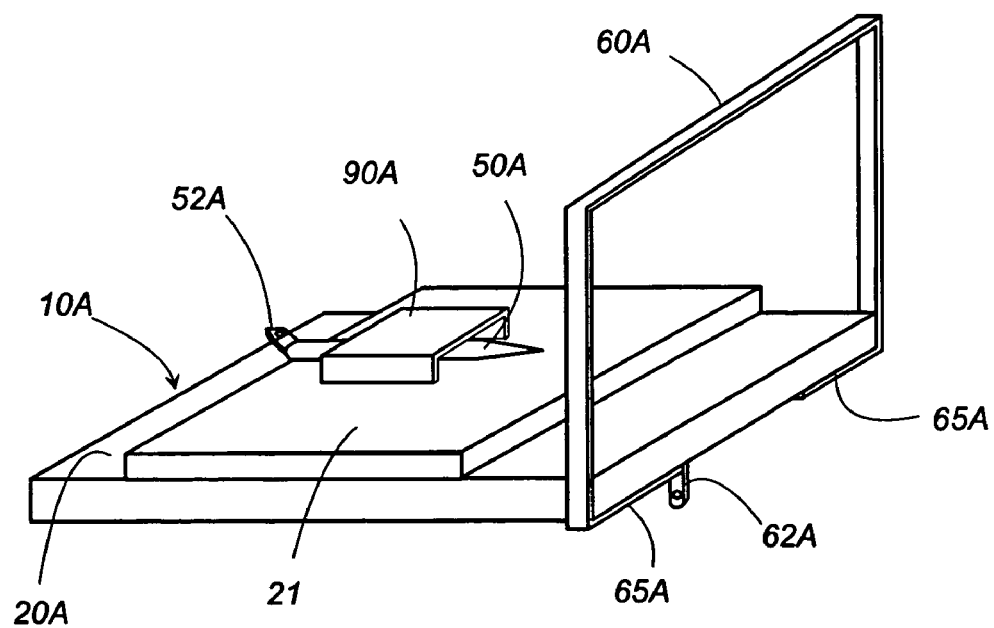

As shown in FIG. 12, the ion generating unit 10A may be modified to include a pair of side ribs 24A of dielectric material at the front end corners on the upper face of the base 20A in an adjacent relation to the ground electrode 60A for elongating the creepage distance between the electrodes 50A and 60A. Further, as shown in FIG. 13, the ion generating unit may be modified to include an additional dielectric plate 21 which is stacked upon the upper face of the base 20A to mount the needle electrode 50A thereon also for elongating the creepage distance.

Figure 14:
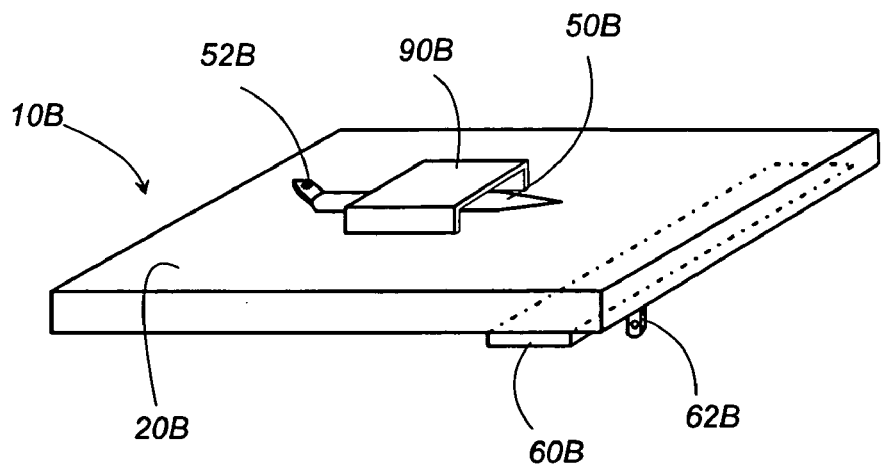

FIG. 14 illustrates an ion generating unit 10B in accordance with a further embodiment of the present invention which is similar to the embodiment of FIGS. 10 and 11 except that a ground electrode 60B is flat shaped and mounted at the front edge on the lower face of the base 20B in a spaced relation from a needle electrode 50B mounted on top face of the base 20B. Like parts are designated by like reference numerals with a suffix letter of "B".

Figure 15:
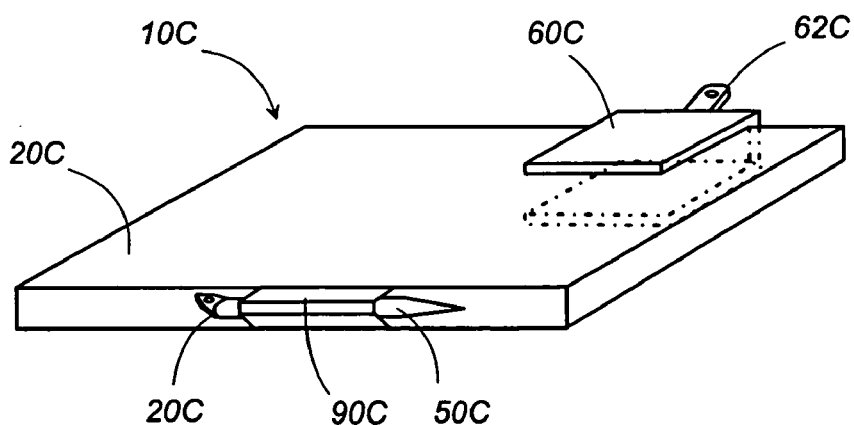
Figure 16:
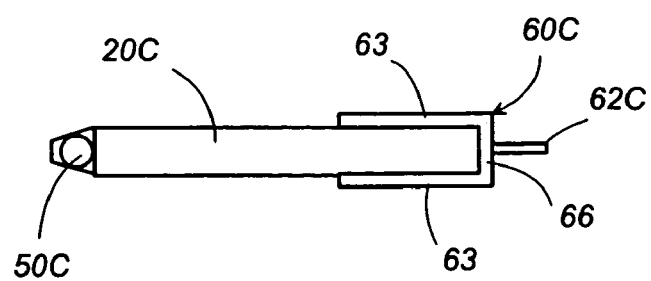
FIG. 16 is a side view of the unit of FIG. 15.

FIGS. 15 and 16 illustrate an ion generating unit 10C in accordance with a still further embodiment of the present invention which is similar to the embodiments of FIGS. 10 and 11, but is configured to mount a needle electrode 50C on one of side faces of a rectangular flat base 20C and mount a ground electrode 60C around the opposite side face of the base 20C. Like parts are designated by like reference numerals with a suffix letter of "C". The ground electrode 60A is a U-shaped member with a pair of yoke plates 63 joined by a web 66 and is mounted on a portion of one lateral end of the base 20C away from the needle electrode 50C with the yoke plates 63 placed upon the upper and lower faces of the base 20C, respectively. A ground electrode 62C extends from the web 66 for connection with a wire leading to the ground of the like high voltage generating circuit.

Figure 17:
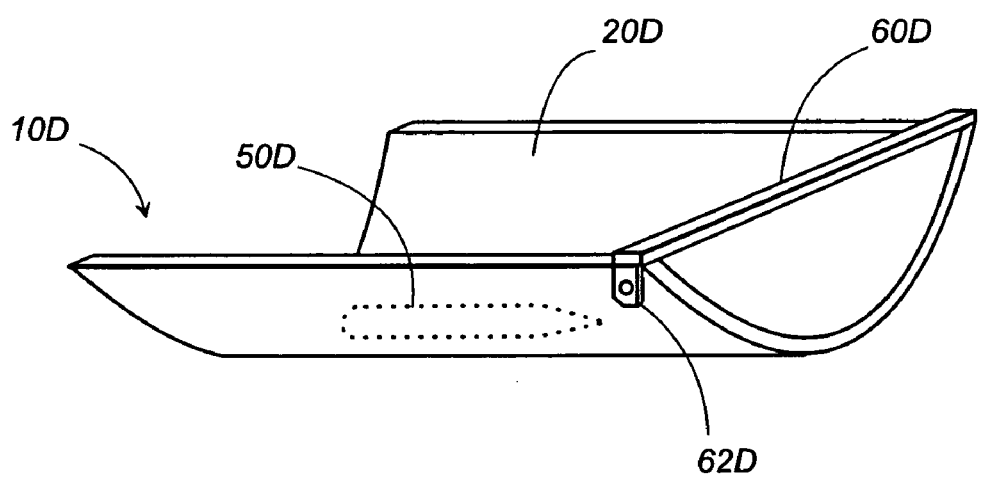
FIGS. 17 and 18 are perspective views respectively illustrating ion generating units respectively in accordance with further embodiments of the present invention.
Figure 18:
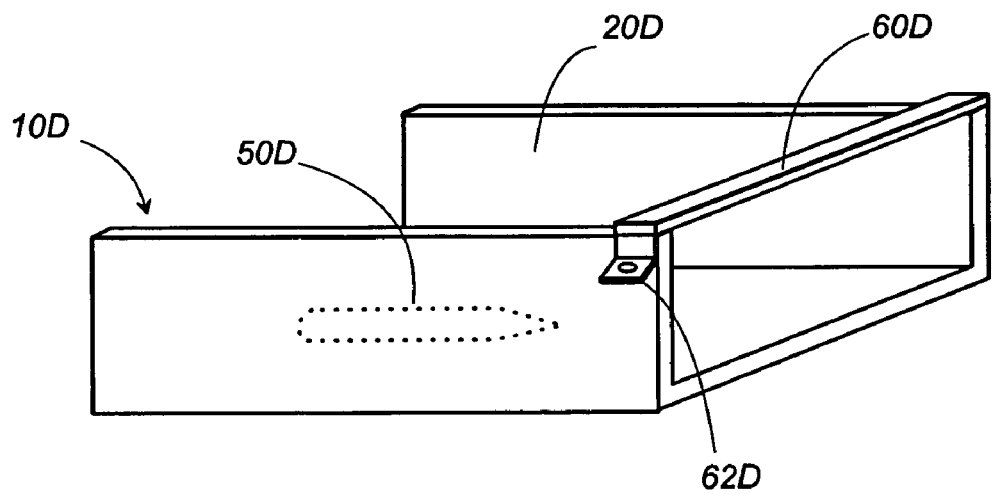

FIG. 17 illustrates an ion generating unit 1 OD in accordance with a further embodiment of the present invention which is similar to the embodiment of FIGS. 10 and 11 except that a dielectric base 20D is shaped into a shallow arcuate configuration. Like parts are designated by like reference numerals with a suffix letter of "D". A needle electrode 50D is mounted on the center of the upper face of the base 20D with its pointed top receded from the front end of the base 20D, whereas a ground electrode 60D spans straight at the front end of the base 20D with its opposite ends fixed to the side faces of the base 20D at portions away from the needle electrode 50D. A ground terminal 62D is bent downward from one end of the ground electrode 60D. Alternatively, the base 20D may be shaped to have parallel side ribs 24D extending from opposite lateral sides of a flat plate 22D, as shown in FIG. 18.

The invention claimed is:
1. An ion generating unit comprising:
a dielectric base having a length and carrying a needle electrode and a ground electrode,
said needle electrode having a pointed tip and being adapted to receive a high electric voltage relative to said ground electrode for electrically charging particles present in the surrounding air,
said needle electrode having a voltage terminal for electrical connection with a voltage output of a high voltage generating circuit,
said ground electrode having a ground terminal for electrical connection with a ground of said high voltage generating circuit;
said dielectric base being a polyhedron having multiple faces including a first face and a second face which are different from each other and have the length of said dielectric base,
said needle electrode being mounted on or in a closely adjacent relation to said first face,
said needle electrode having its pointed tip directing forwardly along the length of said dielectric base with said pointed tip receded from the front end of said dielectric base,
said ground electrode being mounted at said front end of said dielectric base in longitudinally spaced relation with said pointed tip of said needle electrode, and
said ground electrode having anchor ends which are fixed to said second face in such a manner that said ground electrode is secured to said dielectric base only by said anchor ends, one of said anchor ends being with said ground terminal, wherein
said base includes a generally flat plate defining said first and second faces respectively on the upper and lower faces thereof;
said dielectric base further including a pair of side ribs integrally upstanding from lateral edges of said plate,
said ground electrode is an arched member with a pair of inward bents that extend integrally from the lower ends of the arched member to define said anchor ends, said inward bents being fixed to said lower face of said plate with the lower ends of said arched member routing outwardly of said side ribs, respectively.
2. The ion generating unit as set forth in claim 1, wherein said dielectric base is formed on its upper face with a socket for retaining said needle electrode,
said socket having a slot into which said needle electrode is inserted with its pointed tip projecting from said socket,
said slot being defined between a pair of partitions which are integrally supported by said side ribs in an upwardly spaced relation to the upper face of said dielectric base,
said slot being configured to receive the needle electrode in such a manner as to float said needle electrode above the upper face of said base.
3. The ion generating unit as set forth in claim 2, wherein said slot includes a bottom open cavity,
said needle electrode is formed at its longitudinally intermediate portion with a U-shaped bent which is held in said cavity.
4. The ion generating unit as set forth in claim 2 or 3, further including
a dielectric cap which is press-fitted on said socket to fix said needle electrode between said cap and said socket.

* * * * *